United States Patent [19]

Mohacsi et al.

[11] Patent Number: 4,959,359
[45] Date of Patent: Sep. 25, 1990

[54] PHENYL-THIAZEPINONES AS CALCIUM REGULATING AGENTS

[75] Inventors: Erno Mohacsi, Summit; Jay P. O'Brien, Cedar Grove, both of N.J.

[73] Assignee: Hoffmann-La Roche Inc., Nutley, N.J.

[21] Appl. No.: 418,369

[22] Filed: Oct. 6, 1989

[51] Int. Cl.$^5$ .................. C07D 281/06; A61K 31/55
[52] U.S. Cl. ..................................... 514/211; 540/488
[58] Field of Search ......................... 540/488; 514/211

[56] References Cited
U.S. PATENT DOCUMENTS
4,778,790 10/1988 Yanagisawa et al. ............... 540/488

Primary Examiner—Robert T. Bond
Attorney, Agent, or Firm—George M. Gould; Bernard S. Leon; A. Kate Huffman

[57] ABSTRACT

Compounds of the formula

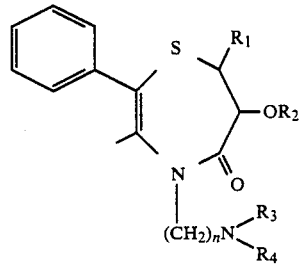

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

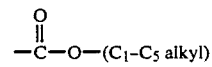

or

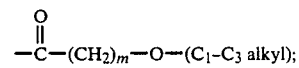

$R_3$ and $R_4$ are independently lower alkyl, phenyl lower alkyl or together form a piperidine or pyrrolidine ring; n is 2 to 4; m is 1 to 2; and pharmaceutically acceptable acid addition salts thereof are described. The compounds of formula I are active as calcium channel blockers and accordingly, are useful as agents for treating ischemia.

27 Claims, No Drawings

PHENYL-THIAZEPINONES AS CALCIUM REGULATING AGENTS

BRIEF SUMMARY OF THE INVENTION

The invention relates to compounds of the formula

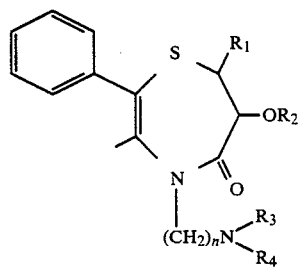

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

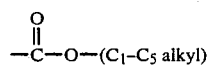

or

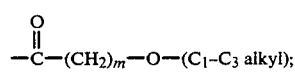

$R_3$ and $R_4$ are independently lower alkyl, phenyl lower alkyl or together form a piperidine or pyrrolidine ring; n is 2 to 4; m is 1 to 2; and pharmaceutically acceptable acid addition salts thereof.

The compounds of formula I are active as calcium channel blockers and accordingly, are useful as agents for treating ischemia.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, and the like. Alternatively, the number of carbon atoms in an alkyl group is designated herein as in "$C_1$–$C_3$ alkyl" which denotes a straight or branched chain alkyl group containing 1 to 3 carbon atoms. The term "lower alkoxy" denotes a straight or branched chain lower alkoxy group containing 1 to 4 carbon atoms, for example, methoxy, ethoxy, propoxy, isopropoxy, butoxy, and the like. The term "halogen" denotes the halogens, that is, bromine, chlorine, fluorine and iodine. The term "lower alkanoyl" denotes a straight or branched chain alkanoyl group of 2 to 5 carbon atoms, for example, acetyl, propionyl, butyryl, isopropionyl and the like. The term "lower cycloalkanoyl" denotes a lower cycloalkanoyl group containing 3 to 6 carbon atoms, for example, cyclopropanoyl, cyclobutanoyl, cyclopentanoyl, and cyclohexanoyl. The term "phenyl lower alkyl" denotes a lower alkyl substituted by a phenyl, for example, phenylmethyl, phenylethyl, phenylpropyl, phenylbutyl and the like.

As used in the formulas herein a solid line ( ▬ ) indicates a substituent that is above the plane of the sulfur and nitrogen containing ring, a dotted line ( ⋯ ) indicates a substituent that is below the plane of the sulfur and nitrogen containing ring. A wavy line ( ∿ ) indicates a substituent whose stereochemistry has not been determined. Alternatively, a wavy line indicates a mixture of compounds with substituents that are epimeric.

The invention relates to compounds of the formula

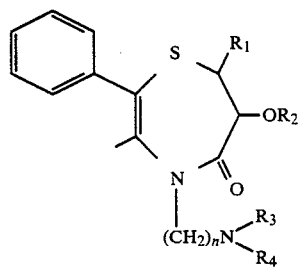

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

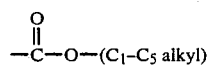

or

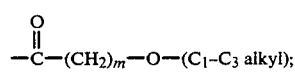

$R_3$ and $R_4$ are independently lower alkyl, phenyl lower alkyl or together form a piperidine or pyrrolidine ring; n is 2 to 4; m is 1 to 2; and pharmaceutically acceptable acid addition salts thereof are described. The compounds of formula I are active as calcium channel blockers and accordingly, are useful as agents for treating ischemia.

The invention also relates to an intermediate compound of the formula

II and to an intermediate compound of the formula

III'

The compounds of formula I contain 2 asymmetric centers at the 6- and 7-positions. Accordingly, the compounds of formula I can be stereoisomers, that is cis or trans isomers.

As used herein, the term "cis" denotes a compound wherein the $R_1$ and $-OR_2$ substituents are both on the same side of the plane of the sulfur and nitrogen containing ring. As used herein the term "(+)-cis" denotes an enantiomer having a relative configuration analogous to that of (+)-cis-6-(acetyloxy)-6,7-dihydro-7-(4-methoxyphenyl)-3-methyl-4-[2-(dimethylamino)ethyl]-2-phenyl-1,4-thiazepin-5(4H) -one which is a (+)-cis compound of the invention.

A compound of the formula

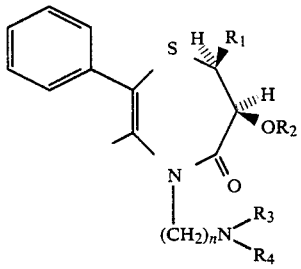

I' wherein $R_1$, $R_2$, $R_3$, $R_4$ and n are as described above is a (+)-cis compound of the invention.

A compound of the formula

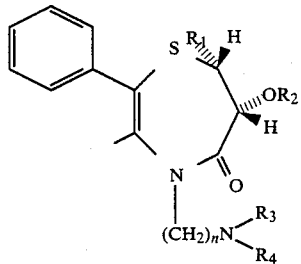

I'' wherein $R_1$, $R_2$, $R_3$, $R_4$ and n are as described above is an enantiomer of a compound of formula I' and a (−)-cis compound of the invention.

Preferred compounds of the invention are cis compounds.

Especially preferred compounds of the invention are (+)-cis compounds.

As used herein the term "trans" denotes a compound of formula I wherein the $R_1$ and $OR_2$ substituents are on opposite sides of the plane of the sulfur and nitrogen containing ring.

A compound of the formula

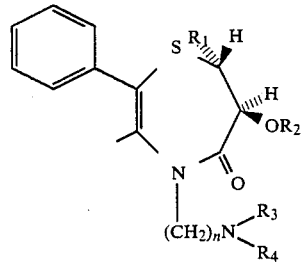

I''' wherein $R_1$, $R_2$, $R_3$, $R_4$, and n are as described above is a trans compound of the invention.

A compound of the formula

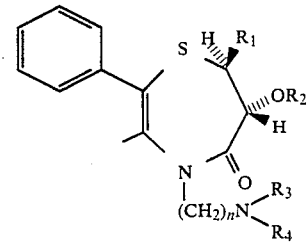

I'$^V$ wherein $R_1$, $R_2$, $R_3$, $R_4$, and n are as described above is the enantiomer of a compound of formula I''', and another trans compound of the invention.

Preferred compounds of formula I are those wherein $R_1$ is 4-lower alkoxyphenyl and $R_2$ is hydrogen or lower alkanoyl, $R_3$ and $R_4$ are independently lower alkyl, and n is 2 to 3. Of these, as has been pointed out above, cis compounds are preferred and (+)-cis compounds are especially preferred.

More preferred compounds of formula I are those wherein $R_1$ is 4-ethoxyphenyl, or more preferably 4-methoxyphenyl.

$R_2$ is propionyl or more preferably hydrogen or acetyl; n is 2; and $R_3$ and $R_4$ are each ethyl or more preferably are each methyl. Of these, as has been pointed above, cis compounds are preferred and (+)-cis compounds are especially preferred. Exemplary of compounds of formula I are:

trans-rac.-6-(acetyloxy)-6,7-dihydro-7-(4-methoxyphenyl)-3-methyl-4-[2-(dimethylamino)ethyl]-2-phenyl-1,4-thiazepin-5(4H)-one;

trans-rac.-6-(acetyloxy)-6,7-dihydro-7-(4-methoxyphenyl)-3-methyl-4-[2-(dimethylamino)ethyl]-2-phenyl-1,4-thiazepin-5(4H)-one hydrochloride;

trans-rac.-6-(hydroxy)-6,7-dihydro-7-(4-methoxyphenyl)-3-methyl -4-[2-(dimethylamino)ethyl]-2-phenyl-1,4-thiazepin-5(4H)-one;

cis-rac.-6-(hydroxy)-6,7-dihydro-7-(4-methoxyphenyl)-3-methyl-4 -[2-(dimethylamino)ethyl]-2-phenyl-1,4-thiazepin-5(4H)-one;

cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one; and cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one (E)-2-butenedioate.

Most preferred compounds of the invention are:
cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one;

cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one (E)-2-butenedioate;

(+)-cis-6-(acetyloxy)-6,7-dihydro-7-(4-methoxyphenyl)-3-methyl-4-[2-(dimethylamino)ethyl]-2-phenyl-1,4-thiazepin-5(4H)-one; and (+)-cis-6-(acetyloxy)-6,7-dihydro-7-(4-methoxyphenyl)-3-methyl-4-[2-(dimethylamino)ethyl]-2-phenyl-1,4-thiazepin-5(4H)-one [S-(R*,R*)]-2,3-dihydroxybutanedioic acid dihydrate.

The invention also relates to intermediates of the formula:

X

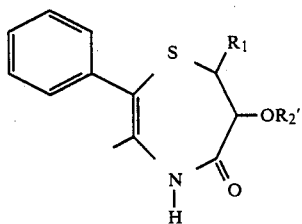

wherein $R_1$ is as described above, and $R_2$' alkyl, lower alkanoyl, lower cycloalkanoyl,

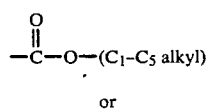

or

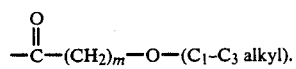

Exemplary of compounds of formula X are:
cis-rac.-6-(acetyloxy)-6,7-dihydro-7-(4-methoxy-phenyl)-3-methyl-2-phenyl-1,4-thiazepin-5(4H)-one; and
trans-rac.-6-(acetyloxy)-6,7-dihydro-7-(4-methoxy-phenyl)-3-methyl-2-phenyl-1,4-thiazepin-5(4H)-one.

The invention also relates to calcium channel blocking compositions comprising an effective amount of a compound of formula I and a pharmaceutically inert carrier material.

The invention also relates to a method of inducing calcium channel blockage, which comprises administering to a warm-blooded animal in need of such treatment an effective amount of a compound of formula I.

The invention also relates to a process for preparing compounds of formula I.

The compounds of formula I can be prepared as shown in Formula Scheme I below:

As used in Formula Scheme I below

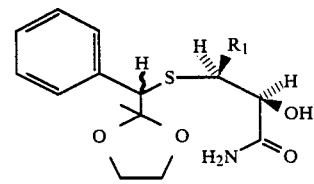

(±)

refers to the (±)-cis compound, that is, the enantiomeric mixture of this cis compound.

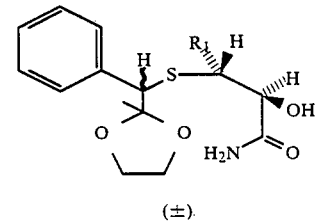

(±)

refers to the (±)-trans compound, that is the enantiomeric mixture of this trans compound. Similar structural formulas have similar meanings throughout these schemes, and throughout this specification. However, solid lines and dotted lines are not used in the structure of the (±)-cis-base of formula Ia* of Formula Scheme II. The drawing used makes clear that the starting compound of formula Ia* is the (±)-cis-base while the final products are the (+)-cis-base and the (−)-cis-base, respectively.

Formula Scheme I

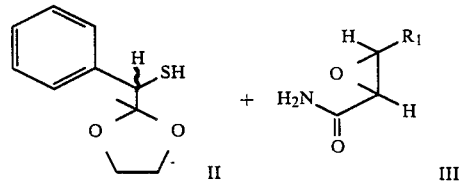
II                III

↓

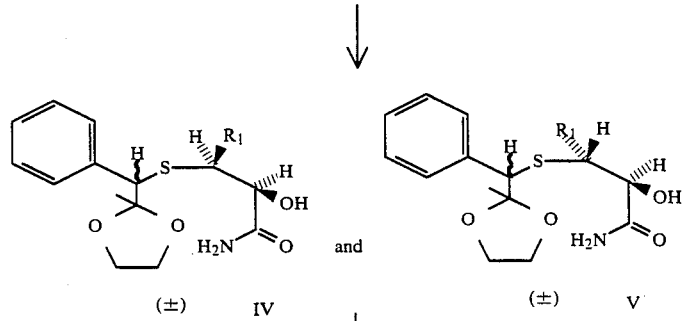
(±) IV      and    (±) V

↓

-continued
Formula Scheme I
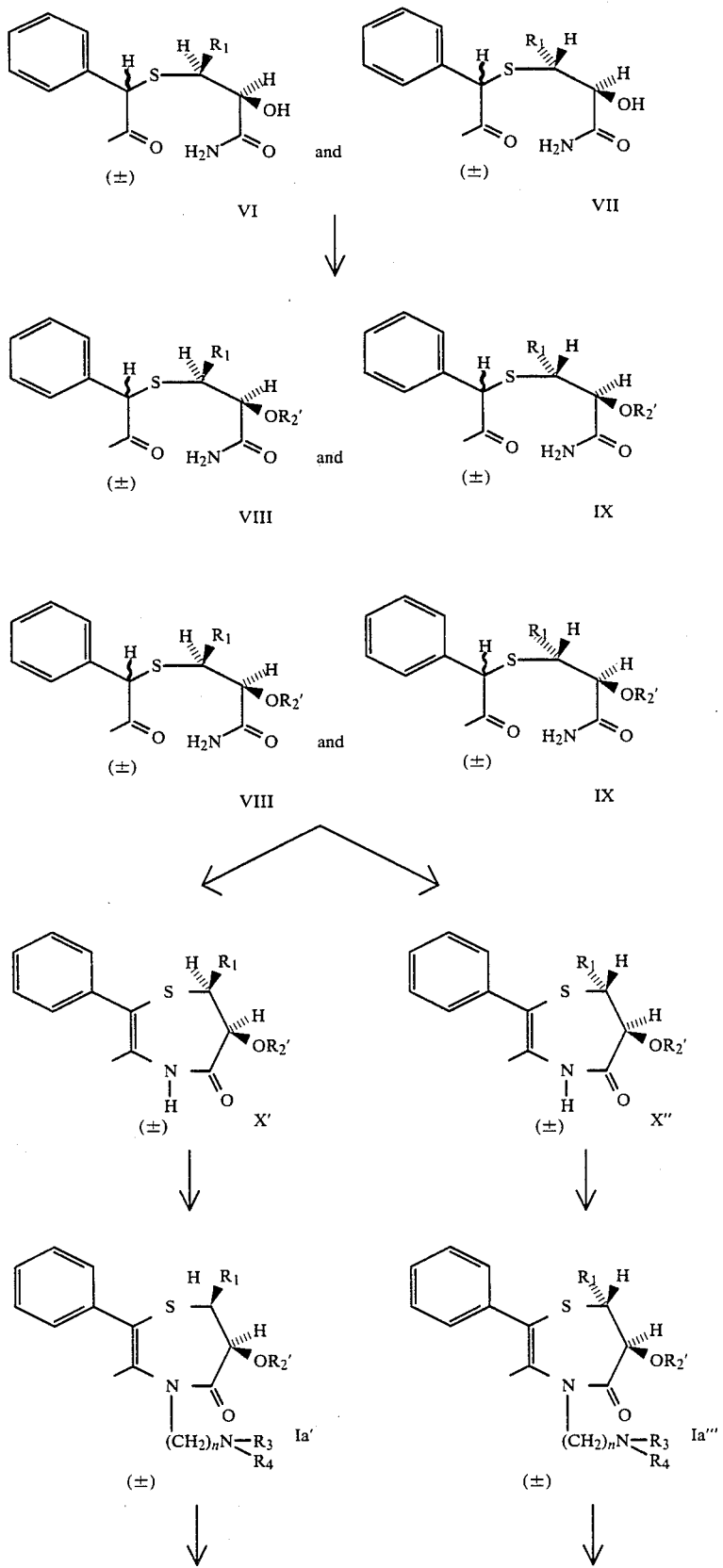

Formula Scheme I

-continued

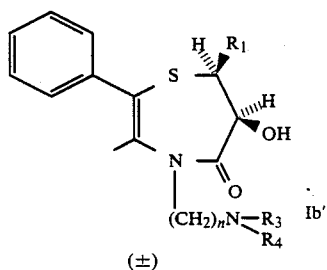 Ib'
(±)

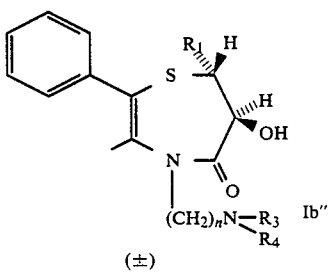 Ib"
(±)

wherein $R_1$, $R_2'$, $R_3$, $R_4$ and n are as described above.

In connection with Formula Scheme I, the compound of formula

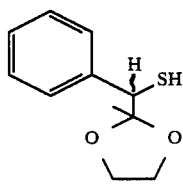 II which can be prepared, as shown in the examples below, is reacted with a compound of formula

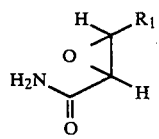 III wherein $R_1$ is as described above which are known or can be prepared in accordance with the examples below, by reaction in a nonpolar aromatic solvent such as ethylbenzene, benzene, or more preferably toluene, at reflux, for a period of 1 to 10 hours, more preferably about 2-3 hours. There is obtained upon chromatographic work-up a mixture of compounds of the formulas:

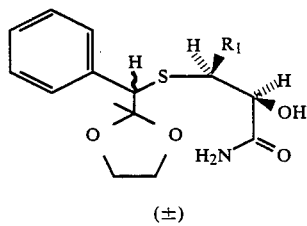 IV
(±)
and

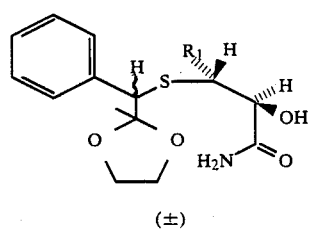 V
(±)

wherein $R_1$ is as described above.

This mixture, without further purification, is deketalized in an aqueous acid solution such as propionic, or more preferably aqueous acetic acid, at a temperature in the range of about 60° C. to about 95° C., more preferably, 85°-95° C. for about 1 to about 10 hours, preferably about 5 to about 7 hours.

Upon conventional work-up, a mixture of compounds of the formulas:

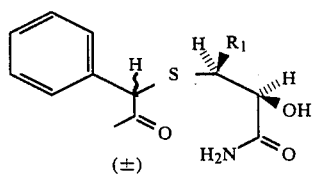 VI
(±)
and

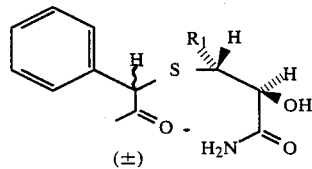 VII
(±)

wherein $R_1$ is as described above is obtained.

Alternatively, this mixture of compounds of formula VI and VII may be prepared directly by the reaction of a compound of formula

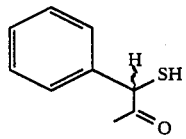 II' with a compound of formula

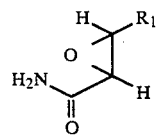 III wherein $R_1$ is as described above in an aromatic organic solvent such as benzene, or more preferably, toluene at reflux, and under an inert atmosphere such as nitrogen.

This mixture, without further purification, is reacted in a combination organic base and an acylating agent. The organic base may be selected from the group consisting of triethylamine, dimethylaniline or, more preferably, pyridine. The acetylating agent will be acetyl, propionyl, or butyryl chloride. Especially preferred as an acylating agent is acetyl chloride.

The reaction is conducted in a polar organic solvent such as chloroform, or, more preferably methylene chloride; at a temperature in the range of about 0°–30°, or more preferably 0°–5° C., for about ½ to about 1 ½ hours. The temperature is allowed to warm to room temperature over a time period of about 1 to about 20 hours.

Following a conventional work-up and chromatography on silica gel, a mixture of compounds of the formulas:

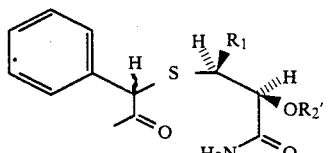

VIII and

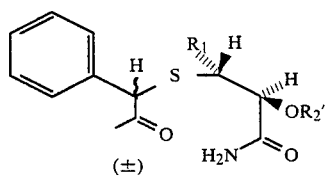

IX wherein $R_1$ and $R_2'$ are as described above is obtained.

This mixture, without further purification, was cyclized in the presence of an organic acid such as p-toluenesulfonic acid in an aromatic organic solvent such as ethylbenzene, toluene, or more preferably benzene, so as to obtain a mixture of compounds of the formula

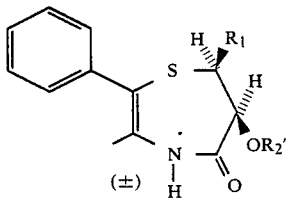

X' and

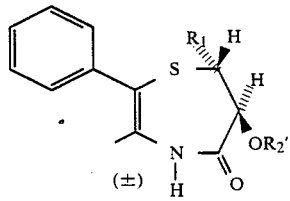

X''' wherein $R_1$ and $R_2'$ are as described above.

Upon work-up, chromatography on, for example, preferably silica gel, and crystallization from a polar organic solvent such as ether a compound of formula X''' may be obtained. From the mother liquor of this crystallization, there may be obtained upon conventional work-up a compound of formula X'.

As can be seen Formula X' and X''' appear on Formula Scheme I. Compounds of formula X' and X''' may be converted to the corresponding compounds of formula Ia' and Ia''' by reaction with a compound of the formula:

XV wherein $R_3$, $R_4$ and n are as described above, and Z is halogen, preferably chlorine.

The reaction is carried out by reacting an alkali metal salt of a compound of formula X', or X''', such as the sodium or more preferably potassium salt thereof with an aminoalkyl halide of formula XV, preferably the chloride thereof, in a polar organic solvent such as, methyl acetate, or more preferably ethyl acetate, at about 40° to about 80°, or at the reflux temperature of the solvent employed, which in the case of ethyl acetate is 77°, for a period of about 1 hour to about 17 hours. The reaction is carried out in the presence of a base, such as, potassium hydroxide in acetone or more preferably potassium carbonate in acetone or in a lower alkyl acetate. Separation of the compound of formula Ia' and Ia''' can be by conventional means such as, crystallization.

A compound of formula Ia' and Ia''' may be hydrolyzed to the corresponding compound of formula Ib' or Ib''' by reaction with an acid such as HCl at room temperature in ethanol, or a base such as sodium hydroxide in ethanol, or potassium carbonate in a polar organic solvent such as methanol, propanol, or ethanol at an elevated temperature. Upon conventional work up the corresponding compound of formula Ib' or Ib''' is obtained.

A compound of formula Ib' and Ib''', which is encompassed by compounds of formula I, can be acylated by reaction with a lower alkanoic anhydride, such as propionic anhydride, acetic anhydride, or a lower alkanoyl halide for example, acetyl, propionyl or butyryl chloride optionally in the presence of a base such as, pyridine, triethylamine, or dimethylaniline at room temperature or up to about 115°.

Alternatively, compounds of formula I wherein $R_2$ is lower alkyl can be obtained by reacting an alkali metal salt of a compound of formula Ib' or Ib''' such as a sodium salt (prepared by reacting a compound of formula Ib' or Ib''' with an alkali metal hydride like sodium hydride), with an alkylating agent such as dialkyl sulfate, more particularly dimethyl sulfate in an aromatic solvent such as toluene or more preferably benzene, at about reflux temperature for a period of about 10 minutes to about 2 hours. The resulting compound of formula I can be isolated by conventional means such as crystallization.

Alternatively, a compound of formula I wherein $R_2$ is

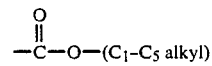

can be obtained by a reaction of a compound of formula Ib' or Ib''' with an alkyl halo formate such as ethyl chloroformate in a basic solvent such as pyridine at about ice bath temperatures. The resulting compound of formula I can be isolated by conventional means such as crystallization.

A compound of formula I wherein $R_2$ is

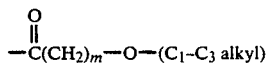

can be prepared by reacting a compound of formula Ib' or Ib''' with an alkoxy alkanoyl halide such as, methoxyacetyl chloride in a basic solvent such as pyridine at about ice bath temperatures. The resulting compound of formula I can be isolated by conventional means such as crystallization.

A compound of formula I wherein $R_2$ is cycloalkyl carbonyl can be obtained by reacting a compound of formula Ib' or Ib''' with a cycloalkylcarboxylic acid halide such as, cyclopropane carboxylic acid chloride in a basic solvent such as pyridine at about ice bath temperatures for about 1 to about 17 hours. The resulting compound of formula I can be isolated by conventional means such as extraction.

A compound of formula I wherein $R_2$ is other than hydrogen can be converted into a corresponding acid addition salt by treatment with an organic acid such as, acetic acid, oxalic acid, malonic acid, tartaric acid, maleic acid, citric acid, lactic acid, malic acid, or fumaric acid and a suitable organic solvent such as, ethyl acetate, acetone, methanol, or ethanol. Alternatively, a compound of formula I wherein $R_2$ is other than hydrogen can be converted into a corresponding acid addition salt by treatment with an inorganic acid such as sulfuric acid, hydrobromic acid, or more preferably hydrochloric acid, except in those instances where the $R_2$ substituent would be cleaved by such treatment. The resulting compound of formula I wherein $R_2$ is hydrogen can be converted into the corresponding acid addition salt by treatment with an organic acid as described above or an inorganic acid such as, hydrochloric acid, in a suitable organic solvent such as ethyl acetate.

Alternatively, prior to the above described conversion of a compound formula Ia' or Ia''' to the other compounds of formula I, and the salt forming steps, a cis compound of formula Ia' which is produced as a racemate can be resolved into its optically active enantiomers. The resolution of a particular cis compound of formula Ia*, that is, cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one is shown in Formula Scheme II. The resolution of other compounds of formula Ia' may require, for example, other conventional resolving agents.

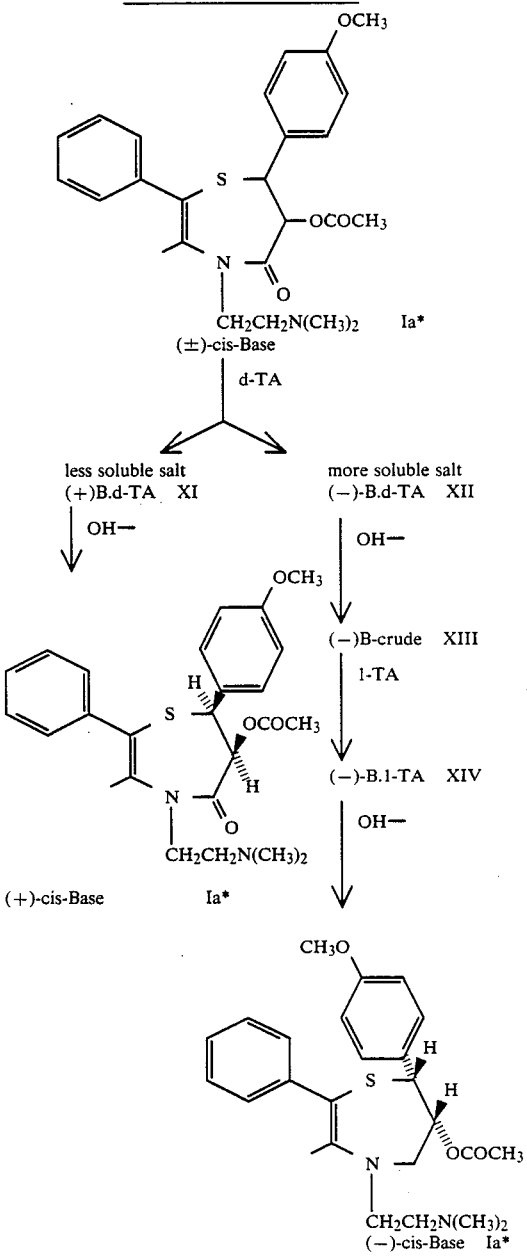

wherein (+)- and (−)B are respectively the (+)- and (−)-enantiomers of the just above-mentioned compound of formula Ia*.

In connection with Formula Scheme II above, the racemate of formula Ia* in a polar protic organic solvent such as methanol is treated with d-tartaric acid, concentrated to dryness, dissolved in warm water, and allowed to crystallize at about room temperature.

The crystals are a salt of formula XI of the resolving agent and the (+)-enantiomer of the compound of formula Ia* of Formula Scheme II. The soluble salt is that of the (−)-enantiomer of the compound of formula Ia* and the resolving agent. This is the solution of formula XII in Formula Scheme II above.

The crystals of the salt of formula XI are collected by filtration.

The crystals of the salt of formula XI can be treated in water with a base such as sodium hydroxide or more preferably concentrated ammonium hydroxide and then the aqueous suspension extracted with an organic solvent such as ethyl acetate and concentrated to obtain the (+)-enantiomer [(+)-cis-Base] of the compound of formula Ia*. This (+)-enantiomer can be used in the above-described reactions of compounds of formula Ia'.

The above solution of the salt of formula XII can be treated in water with a base such as sodium or more preferably dilute ammonium hydroxide, and then the aqueous suspension extracted with an organic solvent such as ethyl acetate, worked up, and concentrated to achieve the (−)-enantiomer of formula XIII.

The (−)-enantiomer of formula XIII can be treated with l-tartaric acid in warm to hot water and allowed to crystallize at room temperature for 2 to 3 days. The salt thus formed is shown as formula XIV in Formula Scheme II above.

This just above-mentioned salt may be dissolved in water and treated with a base such as sodium hydroxide or more preferably dilute ammonium hydroxide and the resulting aqueous suspension can be extracted with an organic solvent such as methylene chloride or more preferably ethyl acetate. The combined extracts can be worked up in a conventional manner to obtain the (−)-enantiomer [(−)-cis-Base] of the compound of formula Ia* of Formula Scheme II. The (−)-enantiomer of the compound of formula Ia* can be used in the above-described reactions of compounds of formula Ia'.

Other cis racemates of formula Ia can be similarly resolved by using other conventional resolving agents.

The compound of formula II is prepared from known starting materials in a manner shown in the examples below.

A compound of formula III is prepared from known starting materials in a manner shown in the examples below.

The compounds of formula XV are known compounds or can be prepared according to known methods. Exemplary of the compounds of formula XV are:
2-dimethylaminoethyl chloride;
2-dimethylaminoethyl bromide;
2-diethylaminoethyl chloride;
2-dipropylaminoethyl chloride; and
3-dimethylaminopropyl chloride.

As can be seen, formula I encompasses, formulas I', I'', I''', $I^{IV}$, Ia', Ia'', Ib', Ib''', and Ia*.

The compounds of formula I, including the pharmaceutically acceptable acid addition salts thereof are calcium antagonists, more specifically, calcium channel blockers, and therefore useful as agents in lowering blood pressure and in treating ischemia. Their pharmacologically useful activities are demonstrated in warm-blooded animals using standard procedures which are set forth below.

The calcium channel blocking activity of compounds of formula I was determined by measuring the effect of compounds of formula I on isolated rat aortic strips.

Contraction of Rat Aortic Strips

Aortas were excised from rats, placed in Krebs-Henseleit solution, modified so as to be calcium free, with a depolarized level of potassium (45 mM), and 0.02 mM EDTA. The aorta was then helically cut into a strip about 2 mm wide. This strip was then divided into four equal segments about 15 mm in length, which were hung in isolated tissue chambers, attached to the appropriate tranducers and subjected to 500 mg basal tension. After a period of stabilization under these conditions, calcium was introduced into the bath and the tissues contracted in a concentration dependent manner.

When no calcium is available in the bathing media, and the potential dependent calcium channels are opened by the high potassium level, contractility is dependent on the level of calcium introduced into the bath. By adding increments of calcium into the bath, a reproducible concentration-dependent contracture can be obtained. Treatment with a calcium channel blocker, such as diltiazem, or a compound of the invention results in an inhibition of this contractile response.

Each number in the table below was derived by first adding calcium alone to tissue and measuring contracture, and then adding calcium to tissue that had been exposed to $3 \times 10^{-7}$M of the compound to be tested and measuring contracture. The number for untreated controls was derived by measuring contracture for two runs where calcium alone was added. As can be seen, contracture was 0.7% greater for the second run of untreated controls.

Diltiazem, after a 15 minute exposure at $3 \times 10^{-7}$M, caused a marked reduction in responsiveness to 2 mM Ca++ when tested in this manner.

A compound tested was placed in the bath at $3 \times 10^{-7}$M for 15 minutes prior to, and during the acquisition of the concentration-dependent curve to calcium for that particular compound. The inhibition in contractile response at 2 mMCa++ was measured as a per cent inhibition as compared to the control. The effects on the 2 mM Ca++ contracture are as follows:

| Compound | % Inhibition | Number of Tests(n) |
|---|---|---|
| Diltiazem | −71.1% | n = 10 |
| Untreated controls | +0.7% | n = 6 |
| A | −73.4% | n = 1 |
| B | −88.3% | n = 1 |
| C | −3.8% | n = 1 |
| D | −13.4% | n = 1 |

In the table above, compound A, for example, inhibited contracture by −73.4% at 2 mM Ca++ as compared to the control. That is, compound A inhibited almost three quarters of the contracture observed for the control at 2 mM Ca++. As used above, compounds A, B, C, and D are as follows:

A=cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one (E)-2-butenedioate:

B=(+)-cis-6-(acetyloxy)-6,7-dihydro-7-(4-methoxyphenyl)-3-methyl-4-[2-dimethylamino)ethyl]-2-phenyl-1,4-thiazepin-5(4H)-one [S-(R*,R*)]-2,3-dihydroxybutanedioic acid hydrate;

C=(−)-cis-6-(acetyloxy)-6,7-dihydro-7-(4-methoxyphenyl)-3-methyl-4-[2-dimethylamino)ethyl]-2-phenyl-1,4-thiazepin-5(4H)-one [R-(R*,R*)]-2,3-dihydroxybutanedioic acid sesquihydrate;

D=trans-rac.-6-(acetyloxy)6,7-dihydro-7-(4-methoxyphenyl)-3-methyl-4-[2-dimethylamino)ethyl]-2-phenyl-1,4-thiazepin-5(4H)-one hydrochloride.

As shown above, all of the compounds of the invention that were tested showed activity in the above test.

The compounds of formula I, and the pharmaceutically acceptable acid addition salts thereof, as herein described, can be incorporated into standard pharmaceutical dosage forms. The compounds of formula I are useful for oral or parenteral application with the usual pharmaceutical carrier materials, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, or capsules, or in liquid form, for example as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The invention also relates to a method of inducing calcium antagonist activity in a warm-blooded animal in need of such treatment which comprises administering an effective amount of a compound of formula I. The invention also relates to a method of lowering blood Pressure or treating ischemia by bringing about myocardial preservation during ischemia, which comprises administering an effective amount of a compound of formula I, or pharmaceutically acceptable acid addition salts thereof to a warm-blooded animal in need of such treatment. The amount of an oral daily dosage can be determined by one skilled in the art and would be comparable to that of diltiazem. The amount of an intravenous dosage can also be determined by one skilled in the art and is comparable to that of diltiazem. It is to be understood, however, that dosages may vary from individual to individual, and accordingly the above recitation is not intended to limit the scope of the present invention in any way.

The following examples further illustrate the invention. All temperatures are in degrees Celsius, unless otherwise mentioned.

EXAMPLE 1

Preparation of α-Chloro-α-phenylacetone

To 6.7 g (0.05 mol) of phenylacetone in a 50 ml round bottom flask equipped with a calcium chloride drying tube was added dropwise 7.0 g (0.052 mol) of sulfuryl chloride over a period of 20 minutes while the temperature of the reaction mixture was maintained at 35°-37° (ice bath cooling of the reaction flask). After the addition was completed the mixture was stirred at room temperature for 1 hour then concentrated at reduced pressure to give 8.3 g (99%) of α-chloro-α-phenylacetone, homogeneous by thin layer chromatography ($CH_2Cl_2$) and was used in the next step without further purification.

EXAMPLE 2

Ethanethioic Acid S-(2-oxo-1-phenylpropyl)ester

To a solution of 3.1 g (0.055 mol) of potassium hydroxide (powdered) in 30 ml of ethanol (absolute) was added 4.2 g (0.055 mol) of thiolacetic acid followed by dropwise addition of 8.3 g (0.05 mol) of α-chloro-α-phenylacetone over a period of 5 minutes while the temperature of the mixture was maintained at 35°-40°. After stirring at room temperature for 1 hour it was diluted with water (about 80 ml, pH is neutral) and the aqueous mixture was extracted with ether. The combined ether extracts were washed with brine, dried ($MgSO_4$), filtered and the solvent was removed under reduced pressure to give 10.6 g (100%) of crude ethanethioic acid S-(2-oxo-1-phenylpropyl)ester which was used without further purification in the next step.

For purification 10.6 g of the above crude product was chromatographed on 150 g of silica gel. The column was eluted with a 75 ml portion of methylene chloride and fractions 6-20 were collected. The solvent was removed under reduced pressure to give 9.4 g (89%) of pure ethanethioic acid S-(2-oxo-1-phenylpropyl)ester. A sample of this compound was crystallized from ether-pet. ether, mp 31°-32°.

EXAMPLE 3 rac.-Ethanethioic Acid-[(2-methyl-1,3-dioxolan-2-yl)phenylmethyl]ester

To a solution of 9.4 g (0.045 mol) of ethanethioic acid S-(2-oxo-1-phenylpropyl)ester and 3.1 g (0.05 mol) of ethylene glycol in 125 ml of benzene was added 1.0 g p-toluenesulfonic acid. The mixture was then heated at reflux over a period of 10 hours while the water formed was removed with the aid of a Dean-Stark trap. The mixture was concentrated under reduced pressure and the residue 11.0 g was chromatographed on 150 g of silica gel. The column was eluted with methylene chloride and fractions 6-20 were collected. Removal of the solvent gave 7.6 g (67%) of rac.-ethanethioic acid-[(2-methyl-1,3-dioxolan-2-yl)phenylmethyl]ester. A sample of this compound was crystallized from pet. ether, mp 49°-52°.

EXAMPLE 4 rac.-2-Methyl-α-phenyl-1,3-dioxolane-2-methanethiol

A solution of 8.0 g (0.032 mol) of rac.-ethanethioic acid-[(2-methyl-1,3-dioxolan-2-yl)phenylmethyl] ester in 140 ml ethanol and 140 ml of aqueous 0.5M potassium carbonate was stirred at room temperature for 20 hours under a nitrogen atmosphere. The mixture was concentrated under reduced pressure to a low volume and extracted with ether. The combined extracts were washed with brine, dried ($MgSO_4$), filtered and the solvent was removed under reduced pressure to give 6.6 g (100%) of crude rac.-2-methyl-α-phenyl-1,3-dioxolane-2-methanethiol. This compound is sensitive to air and therefore the crude product was used immediately for the condensation reaction.

EXAMPLE 5 rac.-1-Mercapto-1-phenyl-2-propanone

Under nitrogen a mixture of 10.6 g (0.05 mol) of ethanethioic acid S-(2-oxo-1-phenylpropyl)ester and 130 ml of 5% sodium hydroxide was stirred rapidly at room temperature for 45 minutes, then extracted with ether. The aqueous mixture was chilled in an ice-bath, acidified with 6N HCl and extracted with ether. The combined organic extracts were washed with brine, dried ($MgSO_4$) and the solvent was removed to give 6.9 g (82%) of crude rac.-1-mercapto-1-phenyl-2-propanone. This compound is sensitive to air and therefore the crude product was used immediately for the condensation reaction.

EXAMPLE 6

Preparation of 3-(4-Methoxyphenyl)oxiranecarboxamide

A mixture of 20.0 g (0.096 mole) of trans-3-(p-methoxyphenyl)glycidate and 200 ml concentrated ammonium hydroxide was stirred at room temperature for 6 hours. The crystals were separated by filtration, washed with water and air dried. For further purification, the crude product was suspended in 150 ml ether (the starting material is ether soluble) and stirred at room temperature for 4 hours, then filtered and air dried to give 12.5 g (67%) of 3-(4-methoxyphenyl)oxiranecarboxamide, mp 165°–167°.

A sample of this compound was recrystallized from ethanol, mp 166°–168°.

EXAMPLE 7

Cis- and trans-rac.-6-(Acetyloxy)-6,7-dihydro-7-(4-methoxyphenyl)-3-methyl-2-phenyl-1,4-thiazeoin-5(4H)-one To a solution of 6.1 g (0.0367 mol) of rac.-1-mercapto-1-phenyl-2-propanone in 75 ml of toluene was added 7.0 g (0.0367 mol) of 3-(4-methoxyphenyl)oxirane carboxamide and the mixture was stirred at reflux under nitrogen for 3.5 hours. The solvent was removed under reduced pressure, then the residue (13.2 g) was dissolved in a small volume of methylene chloride and chromatographed on 160.0 g of silica gel. The column was eluted using a gradual increase of ethyl acetate. Fractions 64–77 (column was eluted with 75 ml portions of 100% ethyl acetate) were collected and removal of the solvent gave 4.1 g of a mixture of racemic erythro- and threo-alcohols.

To the above mixture of 4.1 g (0.011 mol) of alcohols in 130 ml of methylene chloride was added 4.4 ml of pyridine (dried over KOH) followed by dropwise addition of 1.1 g (0.014 mol) of acetyl chloride in 25 ml of methylene chloride over a period of 10 minutes at icebath temperature. After stirring at room temperature the mixture was poured onto ice-water and the aqueous suspension was extracted with methylene chloride. The combined methylene chloride solutions were washed with water then dried (MgSO$_4$) and removal of the solvent gave a residue (4.3 g), which was chromatographed on 64 g of silica gel. The column was eluted with 75 ml portions of a mixture of 90% methylene chloride and 10% ethyl acetate. Fractions 15–24 were combined and the solvent was removed under reduced pressure to afford 1.7 g (39%) of a mixture of racemic erythro- and threo-acetate.

A solution of 1.3 g (0.0032 mol) of the above mixture of racemic erythro- and threo-acetate in 60 ml of toluene containing 0.13 g of p-toluenesulfonic acid was stirred and heated at reflux for 2 hours. The solvent was removed under reduced pressure and the residue (1.5 g) was chromatographed on 30 g of silica gel. The column was eluted with 75 ml portions of a mixture of 90 ml methylene chloride and 10 ml of ethyl acetate. Fractions 16–24 afforded after crystallization from ether 0.2 g (16%) of trans-rac.-6-(acetyloxy)-6,7-dihydro-7-(4-methoxyphenyl)-3-methyl-2-phenyl-1,4-thiazepin-5(4H)-one, mp 179°–180°.

The mother liquor after separation of the racemic trans-amide was concentrated to dryness to give 0.2 g (16%) of pure cis-rac.-6-(acetyloxy)-6,7-dihydro-7-(4-methoxyphenyl)-3-methyl-2-phenyl-1,4-thiazepin-5(4H)-one as an amorphous semihydrate.

EXAMPLE 8 cis-rac.-6-(Acetyloxy)-6,7-dihydro-7-(4-methoxyphenyl)-3-methyl-2-phenyl-1,4-thiazeoin-5(4H)-one To a solution of 1.4 g (0.0066 mol) of rac.-2-methyl-α-phenyl-1,3-dioxolane-2-methanethiol in 20 ml of toluene was added 1.1 g (0.0057 mol) of 3-(4-methoxyphenyl)-oxirane carboxamide and the mixture was stirred at reflux for 2 hours. Removal of the solvent gave a residue which was chromatographed on 35 g of silica gel. The column was eluted with 50 ml portions of ethyl acetate. Fractions 2–11 were combined and concentrated under reduced pressure to give 2.6 g of a mixture of racemic erythro- and threo-ketal, which was used in the next step without further purification. A solution of 5.4 g (0.0133 mol) of a mixture of racemic erythro- and threo-ketal (obtained from two separate runs combined) in 108 ml of acetic acid and 27 ml of water was stirred at 85°–90° for 5.5 hours. The reaction mixture was concentrated at reduced pressure and the residue was fractioned between ethyl acetate and dilute ammonium hydroxide. The combined ethyl acetate solutions were washed with brine, dried (MgSO$_4$) and concentrated to dryness to give 4.8 g (100%) of a mixture of racemic erythro- and threo-ketone, which was used without further purification in the next step.

To a solution of 4.4 g (0.0122 mol) of a mixture of racemic crude erythro- and threo-ketone, chilled in an ice-water bath, was added 6 ml of pyridine followed by dropwise addition of a solution of 1.4 g (0.018 mol) of acetyl chloride in 10 ml of methylene chloride. After stirring in an ice-water bath for 1 hour and then at room temperature for 17 hours, the reaction mixture was diluted with methylene chloride, and water was added to the mixture. The organic solution was washed with 6N HCl then water and dried (MgSO$_4$). Removal of the solvent gave a residue, which was chromatographed on 80 g of silica gel. The column was eluted with 50 ml fractions of a mixture of methylene chloride and ethyl acetate (90:10). Fractions 8 to 25 were combined and the solvents were removed under reduced pressure to give 3.0 g (61%) of a mixture of racemic erythro- and threo-acetate, which was used without further Purification in the next step.

A solution of 5.0 g (0.0125 mol) of a mixture of racemic erythro- and threo-acetate and 0.5 g of p-toluene sulfonic acid in 250 ml benzene was stirred at reflux for 24 hours using a Dean-Stark water trap. The reaction mixture was concentrated to dryness and the residue was chromatographed on 75 g of silica gel. The column was eluted with 75 ml fractions of a mixture of methylene chloride and ethyl acetate (90:10). Fractions 14–25 were combined and the solvent was removed under reduced pressure to afford 2.3 g of a mixture of racemic cis- and trans-amides.

The products of two runs as described above were combined and crystallized from ether to give 5.7 g (40%) of trans-rac.-6-(acetyloxy)-6,7-dihydro-7-(4-methoxyphenyl)-3-methyl-2-phenyl-1,4-thiazepin-5(4H)-one, mp 179°–180°.

The mother liquor after removal of the trans-amide was concentrated to dryness to give 2.3 g (16%) of pure cis-rac.-6-(acetyloxy)-6,7-dihydro-7-(4-methoxyphenyl)-3-methyl-2-phenyl-1,4-thiazepin-5(4H)-one, as an amorphous semihydrate.

EXAMPLE 9 cis-rac.-6-(Acetyloxy)-6,7-dihydro-7-(4-methoxyphenyl)-3-methyl-4-[2-(dimethylamino)ethyl]-2-phenyl-1,4-thiazeoin-5(4H)-one A mixture of 1.7 g (0.0044 mol) of cis-rac.-6-(acetyloxy)-6,7-dihydro-7-(4-methoxyphenyl)-3-methyl-2-phenyl-1,4-thiazepin-5(4H)-one, 0.7 g (0.005 mol) of powdered potassium carbonate and 0.6 g (0.0049 mol) of 2-dimethylaminoethyl chloride in 30 ml of ethyl acetate was stirred at reflux for 2 hours, then twice an additional 0.2 g of dimethylaminoethyl chloride was added at 2 hour intervals. The mixture was heated at reflux for a total of 12 hours, then cooled to room temperature and diluted with water. The organic solution was separated, washed with brine then dried (MgSO$_4$) and the solvent was removed under reduced pressure. The residue was dissolved in acetone and passed through a 10 g silica gel pad which was washed with acetone (12×30 ml). The solvent was evaporated to give 1.8 g (0.039 mol) of crude base which was dissolved in acetone and 0.5 g (0.04 mol) of fumaric acid was added. The resulting crystals were collected to give 1.1 g (44%) cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one (E)-2-butenedioate, mp 176°-177°.

An aliquot of the above salt was dissolved in water, basified with dilute ammonium hydroxide and the aqueous suspension was extracted with ethyl acetate. The organic extracts were washed with brine, dried (MgSO$_4$) and the solvent was removed under reduced pressure. The residue was crystallized from ether to afford cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one, mp 169°-170°.

EXAMPLE 10 cis-rac.-6-Hydroxy-6,7-dihydro-7-(4-methoxyphenyl)-3-methyl-4[2-(dimethylamino)ethyl]-2-phenyl-1,4-thiazeoin-5(4H)-one To a solution of 1.5 g (0.0033 mol) of cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one in 36 ml of ethanol was added 24 ml of 0.5 M potassium carbonate. After the reaction was heated for 1 hour at 70°-80°, it was concentrated to a low volume and extracted with ethyl acetate. The organic extracts were washed with brine, dried (MgSO$_4$) and the solvent was removed under reduced pressure. The residue was crystallized from ether to give 0.9 g (67%) of cis-rac.-6-(hydroxy)-6,7-dihydro-7-(4-methoxyphenyl)-3-methyl-4-[2(dimethylamino)ethyl]-2-phenyl-1,4-thiazepin-5(4H)-one, mp 110°-111°.

EXAMPLE 11 trans-rac.-6-(Acetyloxy)-6,7-dihydro-7-(4-methoxyphenyl)-3-methyl-4-[2-(dimethylamino)ethyl]-2-phenyl-1,4-thiazeoin-5(4H)-one.

A mixture of 2.3 g (0.006 mol) of trans-rac.-6-(acetyloxy)-6,7-dihydro-7-(4-methoxyphenyl)-3-methyl-2-phenyl-1,4-thiazepin-5(4H)-one, 1.0 g (0.0072 mol) of powdered potassium carbonate, and 0.8 g (0.0066 mol) of 2-dimethylaminoethyl chloride in 50 ml of ethyl acetate was stirred and heated at reflux for 2 hours, then twice an additional 0.3 g of dimethylaminoethyl chloride was added at 2 hour intervals. The mixture was heated at reflux for a total of 2 hours, then cooled to room temperature and diluted with water. The organic phase was separated, washed with brine and dried (MgSO$_4$) and the solvent was removed under reduced pressure. The residue was crystallized from ether to give 1.7 g (70%) of trans-rac.-6-(acetyloxy)-6,7-dihydro-7-(4-methoxyphenyl)-3-methyl-4-[2-(dimethylamino)-ethyl]-2-phenyl-1,4-thiazepin-5(4H)-one, mp 119°-120°.

The above base 0.5 g (0.0011 mol), was dissolved in acetone and treated with hydrogen chloride (anhydrous). The resulting crystals were separated to give 0.5 g of trans-rac.-6-(acetyloxy)-6,7-dihydro-7-(4-methoxyphenyl)-3-methyl-4-[2-(dimethylamino)ethyl]-2-phenyl-1,4-thiazepin-5(4H)-one hydrochloride, mp 219°-220°.

EXAMPLE 12 trans-rac.-6-(Hydroxy)-6,7-dihydro-7-(4-methoxyphenyl)-3-methyl-4-[2-(dimethylamino)ethyl]-2-phenyl-1,4-thiazeoin-5(4H)-one To a solution of 1.2 g (0.0026 mol) of trans-rac.-6-(acetyloxy)-6,7-dihydro-7-(4-methoxyphenyl)-4-[2-(dimethylamino)ethyl]-3-methyl-2-phenyl-1,4-thiazepin-5(4H)-one in 36 ml of ethanol was added 24 ml of 0.5 M potassium carbonate. After the reaction was heated at 70°-80° for 1 hour it was concentrated to a low volume and extracted with ethyl acetate. The organic extracts were washed with brine, dried (MgSO$_4$) and the solvent was removed under reduced Pressure. The residue was crystallized from ether to give 0.8 g (75%) of trans-6-(hydroxy)-6,7-dihydro-7-(4-methoxyphenyl)-3-methyl-4-[2-(dimethylamino)ethyl]-2-phenyl-1,4-thiazepin-5(4H)-one, mp 132°-133°.

EXAMPLE 13

Resolution of Racemate (+)-cis-6-(Acetyloxy)-6,7-dihydro-7-(4-methoxyphenyl)-3-methyl-4-[2-(dimethylamino)ethyl]-2-phenyl-1,4-thiazepin(4H)-one [S-(R*,R*)]-2,3-Dihydrobutanedioic acid A solution of 2.4 g (0.0058 mol) of cis-rac.-6-(acetyloxy)-6,7-dihydro-7-(4-methoxyphenyl)-3-methyl -4-[2-(dimethylamino)ethyl]-2-phenyl-1,4-thiazepin-5(4H)-one and 0.87 g (0.0082 mol) of d-tartaric acid in 100 ml of methanol was concentrated to dryness in high vacuum. The residue was dissolved in 60 ml of warm water and allowed to crystallize at room temperature for 17 hours. The crystals were separated by filtration and dried to give 1.2 g of crude product, mp 90°-92°. One recrystallization from 20 ml of water yielded 1.1 g (69%) of pure (+)-cis-6-(acetyloxy)-6,7-dihydro-7-(4-methoxyphenyl)-3-methyl-4-[2-(dimethylamino)ethyl]-2-phenyl-1,4-thiazepin-5(4H)-one [S-(R*R*)]-2,3-dihydrobutanedioic acid hydrate, mp 98°-99°, $[\alpha]_D^{25}+175.26°$ (C 0.57, MeOH).

1.1 g (0.00195 mol) of the above salt, was dissolved in water and decomposed with cold dilute ammonium hydroxide. The aqueous suspension was extracted with ethyl acetate and the combined extracts were washed with brine, dried (MgSO$_4$) and the solvent was removed under reduced pressure to give 0.7 g (88%) of amorphous (+)-cis-6-(acetyloxy)-6,7-dihydro-7-(4-methoxyphenyl)-3-methyl-4-[2-(dimethylamino)ethyl]-2-phenyl-1,4-thiazepin-5(4H)-one as the 0.25 water hydrate, $[\alpha]_D^{25} +187.63°$ (C 0.509, MeoH).

EXAMPLE 14

(−)-cis-6-(Acetyloxy)-6,7-dihydro-7-(4-methoxyohenyl)-3-methyl-4-[2-(dimethylamino)ethyl]-2-phenyl-1,4-thiazeoin-5(4H) -one [R-(R*R*)]-2-Dihydroxybutanedioic Acid The mother liquors obtained in the preparation of (+) -cis-6-(acetyloxy)-6,7-dihydro-7-(4-methoxyphenyl)-3-ethyl-4-[2-(dimethylamino)ethyl]-2-phenyl-1,4-thiazepin-5(4H)-one [S-(R*,R*)]-2,3-dihydroxybutanedioic acid were basified with cold dilute ammonium hydroxide and the aqueous suspension was extracted with ethyl acetate. The combined extracts were washed with brine, dried (MgSO$_4$) and the solvent was removed under reduced pressure. The crude (−)-base 1.9 g (0.0046 mol) was combined with 0.7 g (0.0046 mol) of l-tartaric acid and dissolved in 50 ml of hot water. The solution was allowed to crystallize at room temperature for 48 hours. The crystals were separated by filtration to give 1.1 g (69%) of pure (−)-cis-6-(acetyloxy)-6,7-dihydro-7-(4-methoxyphenyl)-3-methyl-4-[2-(dimethylamino)ethyl]-2-phenyl-1,4-thiazepin-5(4H)-one [R-(R*,R*)]-2,3-dihydroxybutanedioic acid, sesquihydrate, mp 90°–92°, $[\alpha]_D^{25}$ (C 0.51, MeOH).

The above (−)-base l-TA salt, 1.1 g (0.00195 mol), was dissolved in water and basified with cold dilute ammonium hydroxide. The aqueous suspension was extracted with ethyl acetate and the combined extracts were washed with brine, dried (MgSO$_4$) and the solvent was removed under reduced pressure to give 0.7 g (88%) of amorphous (−)-cis-6-(acetyl-oxy)-6,7-dihydro-7-(4-methoxyphenyl)-3-methyl 4-[2-(dimethylamino)ethyl]-2-phenyl-1,4-thiazepin-5(4H)-one 0.25 molar hydrate, $[\alpha]_D^{25}$ −189.86° (C 0.54, MeOH).

EXAMPLE 15

| Parenteral Solution | | |
|---|---|---|
| Item | Ingredient | mg/ml |
| 1. | Compound A | 10 |
| 2. | Benzyl Alcohol | 10 |
| 3. | Sorbitol | 38 |
| 4. | Hydrochloric Acid U.S. to pH | 3-7 |
| 5. | Sodium Hydroxide q.s. to pH | 3-7 |
| 6. | Water for Injection q.s. to | 1 ml |

| Capsule | | mg/Capsule | |
|---|---|---|---|
| Item | Ingredient | 100 mg. | 200 mg |
| 1. | Compound B | 100 | 200 |
| 2. | Corn Starch (Pregelatinized) | 50 | 80 |
| 3. | Modified Starch | 10 | 20 |
| 4. | Talc | 20 | 20 |
| 5. | Magnesium Stearate | 1 | 1 |
| | | 181 mg | 322 mg |

(1) Mix items 1–3 and wet granulate with water. Dry at 45° overnight.
(2) Mill through suitable screen using appropriate milling equipment.
(3) Add items (4) and (5) and mix for five minutes.
(4) Fill into suitable capsule.

As used herein, compounds A and B are as follows:
Compound A is cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one (E)-2-butenedioate.
Compound B is (+)-cis-6-(acetyloxy)-6,7-dihydro-7-(4-methoxyphenyl)-3-methyl-4-[2-dimethylamino)ethyl]-2-phenyl-1,4-thiazepin-5(4H)-one [S-(R*, R*)]-2,3-dihydroxybutanedioic acid hydrate.

We claim:
1. A compound of the formula

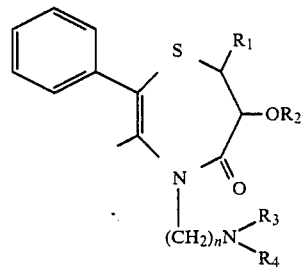

I wherein R$_1$ is phenyl substituted with 1 to 3 substituents selected from the group consisting of halogen and lower alkoxy; R$_2$ is hydrogen, lower alkyl, lower alkanoyl, lower cycloalkanoyl,

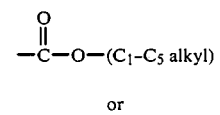

or

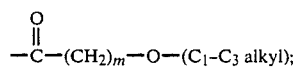

R$_3$ and R$_4$ are independently lower alkyl, phenyl lower alkyl or together form a piperidine or pyrrolidine ring; n is 2 to 4; n is 1 to 2; or a pharmaceutically acceptable acid addition salt thereof.

2. A compound in accordance with claim 1, of the formula

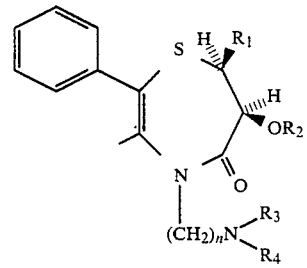

I' wherein R$_1$ is phenyl substituted with 1 to 3 substituents selected from the group consisting of halogen and lower alkoxy; R$_2$ is hydrogen, lower alkyl, lower alkanoyl, lower cycloalkanoyl,

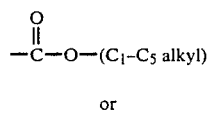

or

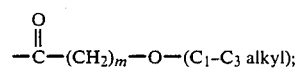

R$_3$ or R$_4$ are independently lower alkyl, phenyl lower alkyl or together form a piperidine or pyrrolidine ring; n is 2 to 4; m is 1 to 2; an enantiomer or a racemate thereof or a pharmaceutically acceptable acid addition salt thereof.

3. A compound in accordance with claim 1, of the formula

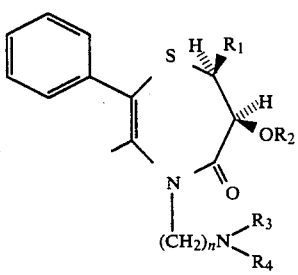

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

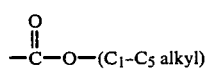

or

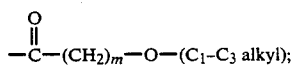

$R_3$ and $R_4$ are independently lower alkyl, phenyl lower alkyl or together form a piperidine or pyrrolidine ring; n is 2 to 4; m is 1 to 2; or a pharmaceutically acceptable acid addition salt thereof.

4. A compound in accordance with claim 3 wherein $R_1$ is 4-lower alkoxyphenyl, $R_2$ is lower alkanoyl, $R_3$ and $R_4$ are independently lower alkyl and n is 2 to 3.

5. A compound in accordance with claim 4, (+)-cis-6-(acetyloxy)-6,7-dihydro-7-(4-methoxyphenyl)-3-methyl-4-[2-(dimethylamino)ethyl]-2-phenyl-1,4-thiazepin-5(4H)-one.

6. A compound in accordance with claim 4, (+)-cis-6-(acetyloxy)-6,7-dihydro-7-(4-methoxyphenyl)-3-methyl -4-[2-(dimethylamino)ethyl]-2-phenyl-1,4-thiazepin-5(4H)-one S-(R*,R*)]-2,3-dihydroxybutanedioic acid dihydrate.

7. A compound in accordance with claim 2 wherein $R_1$ is 4-lower alkoxyphenyl, $R_2$ is lower alkanoyl, $R_3$ and $R_4$ are independently lower alkyl and n is 2 to 3.

8. A compound in accordance with claim 7, cis-rac.-6-(acetyloxy)-6,7-dihydro-7-(4-methoxyphenyl)-3-methyl-4-[2-(dimethylamino)ethyl]2-(dimethylamino)ethyl]-2-phenyl-1,4-thiazepin-5(4H) -one.

9. A compound in accordance with claim 7, cis-rac.-6-(acetyloxy)-6,7-dihydro-7-(4-methoxyphenyl)-3-methyl-4-[2-(dimethylamino)ethyl]-2-phenyl-1,4-thiazepin-5(4H) -one (E)-2-butenedioate.

10. A compound in accordance with claim 2 wherein $R_1$ is 4-lower alkoxyphenyl, $R_2$ is hydrogen, $R_3$ and $R_4$ are independently lower alkyl and n is 2 to 3.

11. A compound in accordance with claim 10, cis-rac.-6-(hydroxy)-6,7-dihydro-7-(4-methoxyphenyl)-3-methyl4-[2-(dimethylamino)ethyl]-2-phenyl-1,4-thiazepin-5(4H)-one.

12. A compound in accordance with claim 1, of the formula

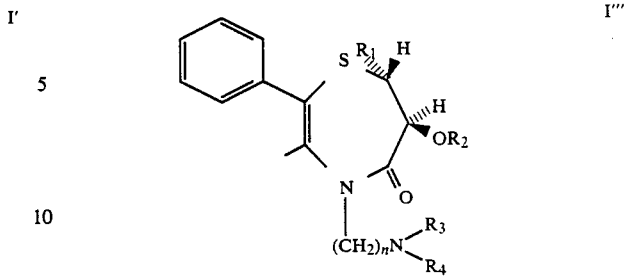

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl,

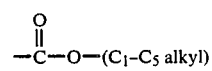

or

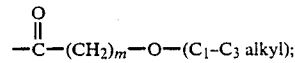

$R_3$ and $R_4$ are independently lower alkyl, phenyl lower alkyl or together form a piperidine or pyrrolidine ring; n is 2 to 4; m is 1 to 2; an enantiomer or racemate thereof or a pharmaceutically acceptable acid addition salt thereof.

13. A compound in accordance with claim 12, wherein $R_1$ is 4-lower alkoxyphenyl, $R_2$ is lower alkanoyl, $R_3$ and $R_4$ are independently lower alkyl and n is 2 to 3.

14. A compound in accordance with claim 13, trans-rac.-6-(acetyloxy)-6,7-dihydro-7-(4-methoxyphenyl)-3-methyl-4-[2-(dimethylamino)ethyl]-2-phenyl-1,4-thiazepin-5(4H) -one.

15. A compound in accordance with claim 13, trans-rac.-6-(acetyloxy)-6,7-dihydro-7-(4-methoxyphenyl)-3-methyl-4-[2-(dimethylamino)ethyl]-2-phenyl-1,4-thiazepin-5(4H) -one hydrochloride.

16. A compound in accordance with claim 12 wherein $R_1$ is 4-lower alkoxyphenyl, $R_2$ is hydrogen, $R_3$ and $R_4$ are independently lower alkyl and n is 2 to 3.

17. A compound in accordance with claim 16, trans-rac.-6-(hydroxy)-6,7-dihydro-7-(4-methoxyphenyl)-3-methyl-4-[2-(dimethylamino)ethyl]-2-phenyl-1,4-thiazepin-5(4H)-one.

18. A calcium channel blocking composition comprising an effective amount of a compound of the formula

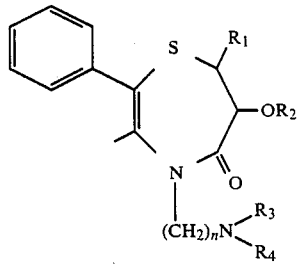

wherein $R_1$ is phenyl substituted with 1 to 3 substituents selected from the group consisting of halogen and lower alkoxy; $R_2$ is hydrogen, lower alkyl, lower alkanoyl, lower cycloalkanoyl, $$-\overset{O}{\underset{\|}{C}}-O-(C_1-C_5 \text{ alkyl})$$

or $$-\overset{O}{\underset{\|}{C}}-(CH_2)_m-O-(C_1-C_3 \text{ alkyl});$$

$R_3$ and $R_4$ are independently lower alkyl, phenyl lower alkyl or together form a piperidine or pyrrolidine ring; n is 2 to 4; m is 1 to 2; or a pharmaceutically acceptable acid addition salt thereof and a pharmaceutically inert carrier material.

19. A composition in accordance with claim 18, wherein $R_1$ is 4-lower alkoxyphenyl, $R_2$ is lower alkanoyl, $R_3$ and $R_4$ are independently lower alkyl and n is 2 to 3.

20. A composition in accordance with claim 19 wherein the compound of formula I is cis-rac.-6-(acetyloxy)-6,7-dihydro-7-(4-methoxyphenyl)-3-methyl-4-[2-(dimethylamino)ethyl]-2-phenyl-1,4-thiazepin-5(4H)-one or the (E)-2-butenedioate thereof.

21. A method of inducing calcium channel blockage, which comprises administering to a warm-blooded animal in need of such treatment an effective amount of a compound of the formula

I wherein $R_1$ is phenyl substituted with 1 to 3 substituents selected from the group consisting of halogen and lower alkoxy; $R_2$ is hydrogen, lower alkyl, lower alkanoyl, lower cycloalkanoyl, $$-\overset{O}{\underset{\|}{C}}-O-(C_1-C_5 \text{ alkyl})$$

-continued or $$-\overset{O}{\underset{\|}{C}}-(CH_2)_m-O-(C_1-C_3 \text{ alkyl});$$

$R_3$ and $R_4$ are independently lower alkyl, phenyl lower alkyl or together form a piperidine or pyrrolidine ring; n is 2 to 4; m is 1 to 2; or a pharmaceutically acceptable acid addition salt thereof.

22. A method in accordance with claim 21 wherein $R_1$ is lower alkoxyphenyl, $R_2$ is lower alkanoyl, $R_3$ and $R_4$ are independently lower alkyl, and n is 2 to 3.

23. A method in accordance with claim 22, wherein the compound of formula I is cis-rac.-6-(acetyloxy)-6,7dihydro-7-(4-methoxyphenyl)-3-methyl-4-[2-(dimethylamino)ethyl]-2-phenyl-1,4-thiazepin-5(4H)-one, or the (E)-2-butenedioate salt thereof.

24. A compound of the formula

X wherein $R_1$ is phenyl substituted with 1 to 3 substituents selected from the group consisting of halogen and lower alkoxy; $R_2'$ is lower alkyl, lower alkanoyl, lower cycloalkanoyl, $$-\overset{O}{\underset{\|}{C}}-O-(C_1-C_5 \text{ alkyl})$$

or $$-\overset{O}{\underset{\|}{C}}-(CH_2)_m-O-(C_1-C_3 \text{ alkyl});$$

wherein m is 1 to 2.

25. A compound in accordance with claim 24, where $R_2'$ lower alkanoyl.

26. A compound in accordance with claim 25, cis-rac.-6-(acetyloxy)-6,7-dihydro-7-(4-methoxyphenyl)-3-methyl-2-phenyl-1,4-thiazepin-5(4H)-one.

27. A compound in accordance with claim 25, trans-rac.-6-(acetyloxy)-6,7-dihydro-7-(4-methoxyphenyl)-3-methyl-2-phenyl-1,4-thiazepin-5(4H)-one.

* * * * *